United States Patent
Lu et al.

(10) Patent No.: US 10,350,037 B2
(45) Date of Patent: Jul. 16, 2019

(54) SAWTOOTH WAVE SURFACE DETECTION IN 3D DENTAL RECONSTRUCTION SYSTEM

(71) Applicant: Carestream Health, Inc., Rochester, NY (US)

(72) Inventors: Yanbin Lu, Shanghai (CN); Dawei Sun, Shanghai (CN); Qinran Chen, Shanghai (CN)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 15/640,918

(22) Filed: Jul. 3, 2017

(65) Prior Publication Data
US 2018/0318051 A1    Nov. 8, 2018

Related U.S. Application Data (60) Provisional application No. 62/502,955, filed on May 8, 2017.

(51) Int. Cl.
| | |
|---|---|
| *A61B 1/24* | (2006.01) |
| *A61C 9/00* | (2006.01) |
| *G06K 9/62* | (2006.01) |
| *G06T 5/00* | (2006.01) |
| *G06T 7/11* | (2017.01) |
| *G06T 7/262* | (2017.01) |

(52) U.S. Cl.
CPC ............ *A61C 9/006* (2013.01); *A61B 1/24* (2013.01); *G06K 9/6215* (2013.01); *G06T 5/002* (2013.01); *G06T 7/11* (2017.01); *G06T 7/262* (2017.01); *G06T 2207/20056* (2013.01); *G06T 2207/30036* (2013.01)

(58) Field of Classification Search
CPC ........... A61C 9/006; A61B 1/24; G06T 7/262; G06T 7/11; G06T 5/002; G06T 2207/20056; G06T 2207/30036; G06K 9/6215

See application file for complete search history.

(56) References Cited

U.S. PATENT DOCUMENTS

| | | | |
|---|---|---|---|
| 5,372,502 A | 12/1994 | Massen et al. | |
| 5,966,678 A * | 10/1999 | Lam ................. | G01S 7/4802 356/73 |
| 6,885,464 B1 | 4/2005 | Pfeiffer et al. | |

(Continued)

FOREIGN PATENT DOCUMENTS

WO    2011/145799    11/2011

*Primary Examiner* — Fernando Alcon (57) ABSTRACT

A method for intraoral imaging acquires structured light images from a region of interest and forms a range image that characterizes the surface contour of the region of interest according to the acquired structured light images. At least one row of pixels in the range image is processed by selecting a segment of the row, computing residual noise in the selected segment, generating a template for the segment, wherein the template is characteristic of an imaging artifact related to motion, computing a similarity factor according to correlation between frequency-domain transforms of the template and computed residual noise and comparing the computed similarity factor against a threshold to identify an image artifact. The image artifact or excessive motion are reported.

12 Claims, 10 Drawing Sheets

(56) References Cited

U.S. PATENT DOCUMENTS

| | | | |
|---|---|---|---|
| 7,312,924 B2 | 12/2007 | Trissel | |
| 9,025,867 B2 * | 5/2015 | Cote | G06T 3/4015 |
| | | | 382/162 |
| 9,488,469 B1 * | 11/2016 | Michael | G01B 11/25 |
| 2001/0038705 A1 * | 11/2001 | Rubbert | A61C 7/00 |
| | | | 382/128 |
| 2007/0086762 A1 | 4/2007 | O'Keefe et al. | |
| 2010/0182462 A1 * | 7/2010 | Utsugi | H04N 5/357 |
| | | | 348/241 |
| 2013/0120532 A1 | 5/2013 | Milch | |
| 2013/0120533 A1 | 5/2013 | Milch | |
| 2013/0321673 A1 * | 12/2013 | Lim | G06T 1/20 |
| | | | 348/241 |
| 2013/0321677 A1 * | 12/2013 | Cote | H04N 5/217 |
| | | | 348/243 |

\* cited by examiner

FFT results:
1D row profile and corresponding template,
nominal surface, without movement

SAWTOOTH WAVE SURFACE DETECTION IN 3D DENTAL RECONSTRUCTION SYSTEM

CROSS REFERENCE TO RELATED APPLICATIONS

This application claims priority to U.S. Patent Application Ser. No. 62/502,955, filed May 8, 2017, in the name of Lu et al., and entitled SAWTOOTH WAVE SURFACE DETECTION IN 3D DENTAL RECONSTRUCTION SYSTEM, which is hereby incorporated by reference in its entirety.

TECHNICAL FIELD

The disclosure relates generally to the field of dental imaging and more particularly relates to a method for improved surface characterization of teeth and other intraoral features.

BACKGROUND

Surface contour imaging uses patterned or structured light and triangulation to obtain surface contour information for an object. In contour imaging, a pattern of lines or other features is projected toward the surface of an object from a given angle. The projected pattern on the surface is then viewed from another angle as a contour image, taking advantage of triangulation in order to analyze surface information and to characterize the surface contour based on the deformed appearance of the projected lines. Phase shifting, in which the projected line pattern is incrementally spatially shifted for obtaining additional measurements at higher resolution, helps to more accurately map the object's surface.

Surface contour imaging using structured light has been employed in a number of applications for determining the shape of solid, highly opaque objects. Contour imaging has also been used for characterizing the surface shape of portions of the anatomy and for obtaining detailed data about skin structure. However, a number of technical obstacles complicate effective use of contour projection imaging of the tooth. Among recognized problems for surface contour imaging of teeth are tooth translucency, high reflection levels, and the complex structure of the teeth itself.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but requiring application of a fluorescent coating for operation. Similarly, U.S. Pat. No. 6,885,464 entitled "3-D Camera for Recording Surface Structures, in Particular for Dental Purposes" to Pfeiffer et al. discloses a dental imaging apparatus using triangularization but also requiring the application of an opaque powder to the tooth surface for imaging. U.S. Pat. No. 6,885,464 to Pfeiffer et al. describes an intraoral camera that provides a group of light beams for imaging. Patent Application WO 2011/145799 by Lim describes a 3-D scanner using scanned laser light.

At least one problem that presents an inherent difficulty for surface contour imaging of the teeth relates to the challenge of scanning surfaces within the confined space of the patient's mouth. It can be difficult to position the intraoral camera in a comfortable and stable position for imaging, to retain the scanner in place and/or to reduce or minimize operator or patient movement or fixture vibration while the contour images are being acquired. As a result of unintentional movement during scanning, various types of image artifacts can be generated, compromising the overall accuracy of surface reconstruction, affecting the appearance, and/or affecting the smoothness of the final mesh surface that is typically generated.

Thus, it can be appreciated that there would be benefits to an optical apparatus and method for intraoral surface contour imaging that detects and reports image artifacts resulting from relative movement between the intraoral camera and the subject teeth and other features.

SUMMARY

It is an object of the present invention to advance the art of structured light imaging for intraoral surface contour characterization.

Exemplary method and/or apparatus embodiments herein can improve a capability for reduction of imaging artifacts related to camera or patient movement. Among advantages offered by apparatus and method embodiments of the present invention is a capability for automated detection of imaging artifacts related to camera or patient movement.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

According to one aspect of the disclosure, there is provided a method for intraoral imaging comprising:
a) acquiring a plurality of structured light images from a region of interest and forming a range image that characterizes the surface contour of the region of interest according to the acquired structured light images;
b) processing at least one row of pixels in the range image by:
   (i) selecting a segment of the row;
   (ii) computing residual noise in the selected segment;
   (iii) generating a template for the segment, wherein the template is characteristic of an imaging artifact related to motion;
   (iv) computing a similarity factor according to correlation between frequency-domain transforms of the template and computed residual noise;
   (v) comparing the computed similarity factor against a threshold to identify an image artifact; and
c) reporting the image artifact or excessive motion.

BRIEF DESCRIPTION OF THE DRAWINGS

The foregoing and other objects, features, and advantages of the invention will be apparent from the following more particular description of exemplary embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

DESCRIPTION OF EXEMPLARY EMBODIMENTS

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "structured light illumination" or "patterned illumination" are used to describe the type of projected illumination that is used for surface imaging, range imaging, or "contour" imaging that characterizes tooth shape. The structured light pattern itself can include, as patterned light features, one or more lines, circles, curves, or other geometric shapes that are distributed over the area that is illuminated and that have a predetermined spatial and temporal frequency. One exemplary type of structured light pattern that is widely used for contour imaging is a pattern of evenly spaced lines of light projected onto the surface of interest.

In the context of the present disclosure, the terms "structured light image" and "contour image" are considered to be equivalent and refer to the image that is captured during projection of the light pattern that is used for characterizing the tooth contour. The term "fringe image" can also be used for the structured light image. The term "range image" refers to image content generated using this light pattern that models surface structure.

Two lines of light, portions of a line of light, or other features in a pattern of structured illumination can be considered to be substantially "dimensionally uniform" when their line width is the same over the length of the line to within no more than +/−15 percent. As is described in more detail subsequently, dimensional uniformity of the pattern of structured illumination is used to maintain a uniform spatial frequency.

In the context of the present disclosure, the term "optics" is used generally to refer to lenses and other types of refractive, diffractive, and reflective components used for shaping a light beam. A light-directing or shaping component in this class is termed an "optic".

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

Figure 1:
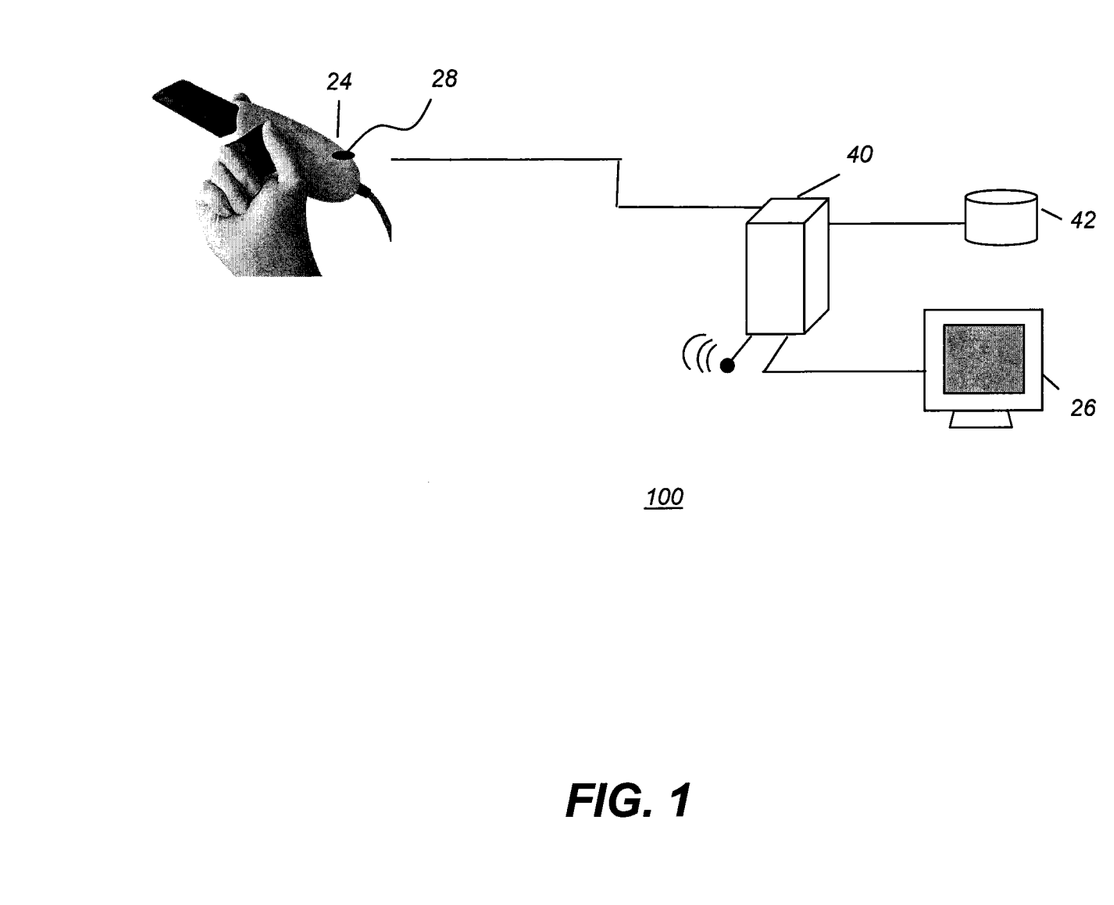
FIG. 1 shows an intra-oral imaging apparatus for contour imaging of teeth.

The schematic diagram of FIG. 1 shows an intraoral imaging system 100 having an intraoral camera apparatus 24 that serves as a scanner for projecting structured light onto the surface of the tooth or other intraoral feature. Camera apparatus 24 is in signal communication, over a wired or wireless data communication channel, with a computer 40 that obtains the images from the projected structured light pattern. Computer 40 processes the images and provides output image data that can be stored as a data file and displayed on a display 26. Computer 40 can be separate from the apparatus 24 probe or may be integrated with the probe, such as for providing some portions of the image processing and results reporting described herein. Computer 40 can also store and retrieve image data with a memory 42 that is in signal communication with computer 40, such as in communication along a network. Camera apparatus 24 can have an audible or visual indicator 28 for reporting excessive motion.

Figure 2A:
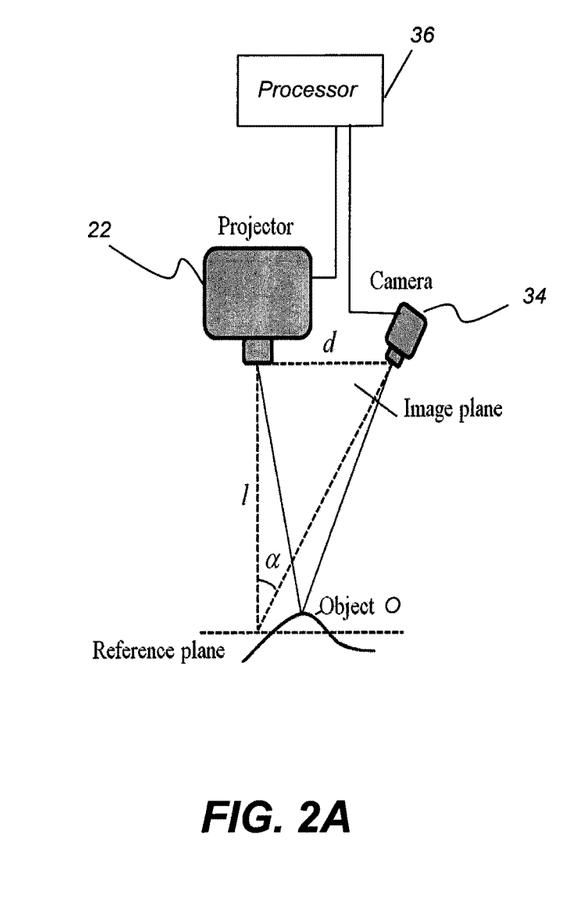
FIG. 2A is a schematic diagram that shows how triangularization is used to obtain surface contour data.
Figure 2B:
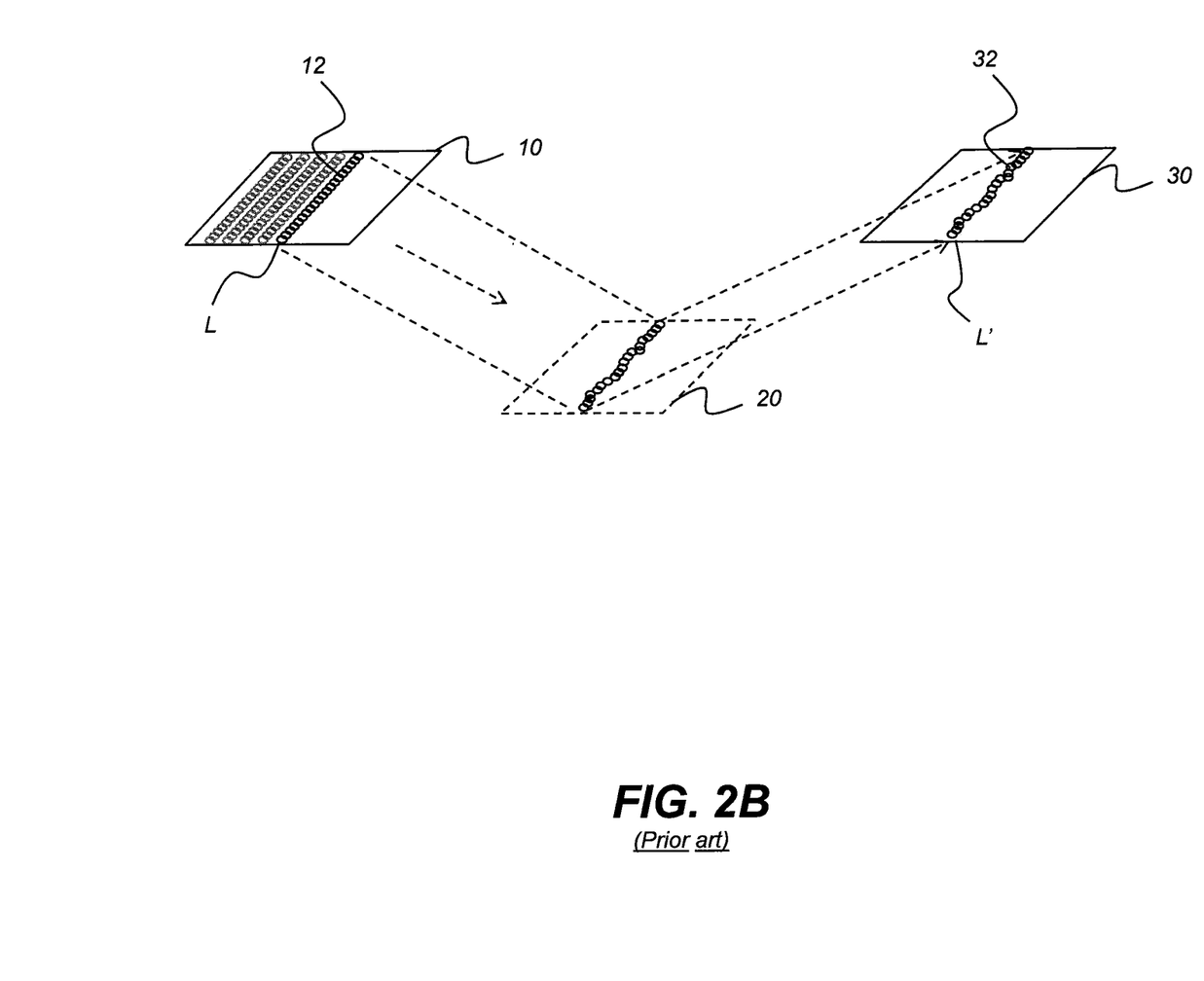
FIG. 2B is a schematic diagram that shows how patterned light is used for obtaining surface contour information.

The schematic diagrams of FIGS. 2A and 2B show how triangularization is used to obtain surface contour data. Provided within the chassis of camera apparatus 24 shown in FIG. 1, a projector 22 and a camera 34, separated by a distance d, cooperate to scan the surface contour. According to an exemplary embodiment of the present disclosure, projector 22 directs successive lines of illumination over a distance l onto the object O at a reference plane. Camera 34, at the image plane, acquires image content corresponding to each projected line. A control logic processor 36, such as a computer, dedicated microprocessor, or other logic processing device, synchronizes operation of projector 22 and camera 34 and obtains, stores, and processes or transmits the acquired image data from camera 34 in order to characterize the surface contour of object O. An angle α is representative of the difference in orientation between camera 34 and projector 22.

The schematic diagram of FIG. 2B shows, with the example of a single line of light L, how patterned light is used for obtaining surface contour information. A mapping is obtained as an illumination array 10 directs a pattern of light from projector 22 (FIG. 2A) onto a surface 20 and a corresponding image of a line L' is formed on an imaging sensor array 30 of camera 34. Each pixel 32 on imaging sensor array 30 maps to a corresponding pixel 12 on illumination array 10 according to modulation by surface 20. Shifts in pixel position, as represented in FIG. 2B, yield useful information about the contour of surface 20. It can be appreciated that the basic pattern shown in FIG. 2B can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using a Digital Light Processor (DLP) device, an integrated array of micromirrors from Texas Instruments, Inc., Dallas, Tex.

By projecting and capturing images that show structured light patterns that duplicate the arrangement shown in FIG. 2B multiple times, the image of the contour line on the camera simultaneously locates a number of surface points of the imaged object. This speeds the process of gathering many sample points, while the plane of light (and usually also the receiving camera) is laterally moved in order to "paint" some or all of the exterior surface of the object with the plane of light.

Multiple structured light patterns can be projected and analyzed together for a number of reasons, including to increase the density of lines for additional reconstructed points and to detect and/or correct incompatible line sequences. Use of multiple structured light patterns is described in commonly assigned U.S. Patent Application Publications No. US 2013/0120532 and No. US 2013/0120533, both entitled "3D INTRAORAL MEASUREMENTS USING OPTICAL MULTILINE METHOD" and incorporated herein in their entirety.

Figure 3:
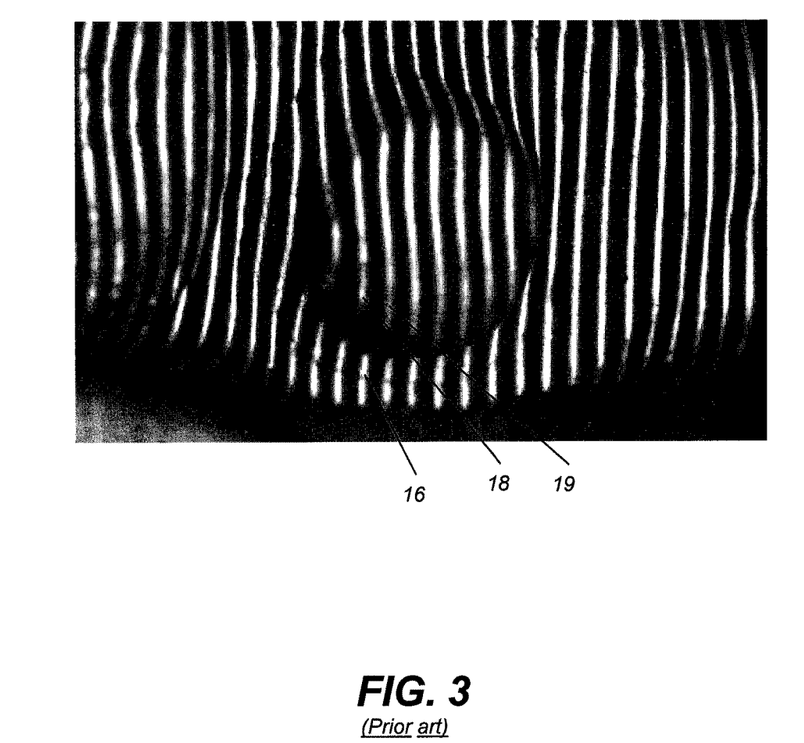
FIG. 3 is a diagram that shows surface imaging using a pattern with multiple lines of light.

FIG. 3 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult over portions of the surface to determine whether line segment 16 is from the same line of illumination as line segment 18 or adjacent line segment 19.

Figure 4A:
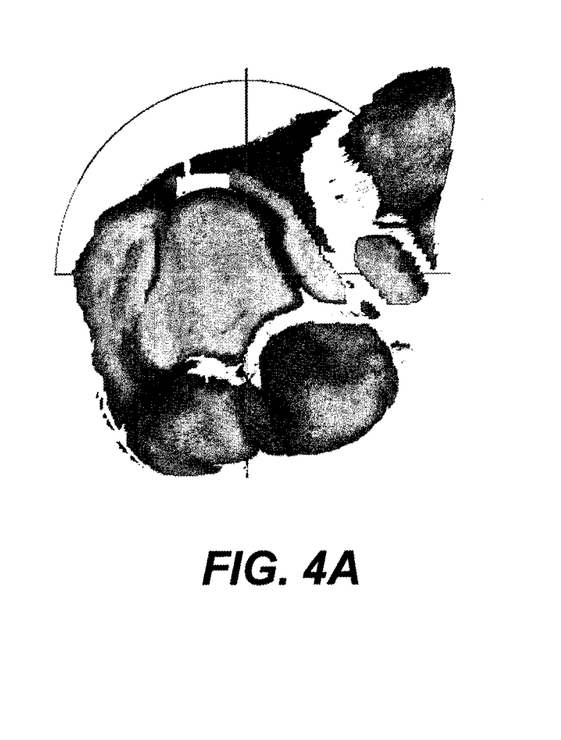
FIG. 4A is an image that shows a mesh obtained from surface contour imaging using structured light.
Figure 4B:
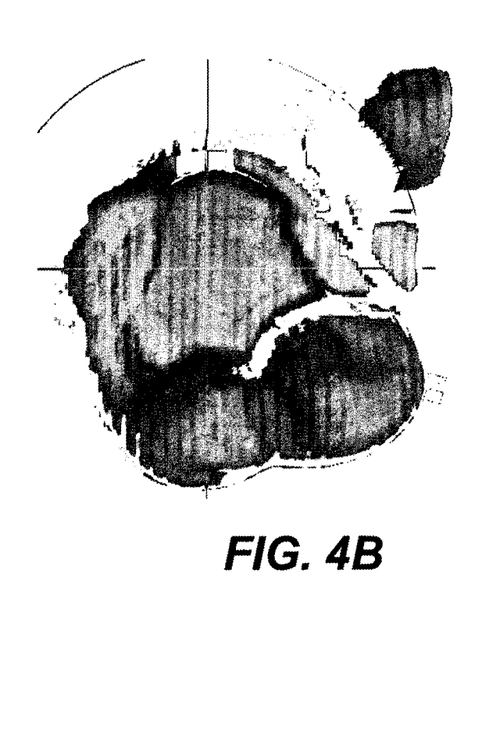
FIG. 4B is an image that shows a mesh obtained from surface contour imaging using structured light and that shows a motion artifact.

Certain exemplary method and/or apparatus embodiments of the present application can address the need for automatically identifying an image artifact in the reconstructed surface contour image caused by inadvertent, relative motion between the intraoral camera and the subject tooth or other intraoral feature. FIG. 4A is an image that shows a mesh generated for a tooth, wherein the mesh data is obtained from surface contour imaging using structured light. There are no perceptible image artifacts in the reconstructed mesh of FIG. 4A. By contrast, FIG. 4B is an image that shows a mesh obtained from surface contour imaging using structured light, wherein the mesh exhibits a common motion artifact. The "sawtooth" or "corrugated" appearance of the tooth surface from the mesh of FIG. 4B is caused by movement during capture of the series of structured light images that are obtained for surface characterization.

The image artifact of FIG. 4B is clearly perceptible to the viewer following 3D surface reconstruction and can be misleading to the viewer or can introduce error in any subsequent processing using the 3D mesh. However, there would be significant advantages in detecting and/or reporting a pronounced artifact such as that shown prior to attempting to use the resulting mesh image for further analysis and processing. Early detection of this problem could prompt the user to re-attempt contour imaging for the affected area while the patient is still seated, for example obviating the need and expense of a patient recall should the resulting image be unusable.

Figures 5A, 5B:
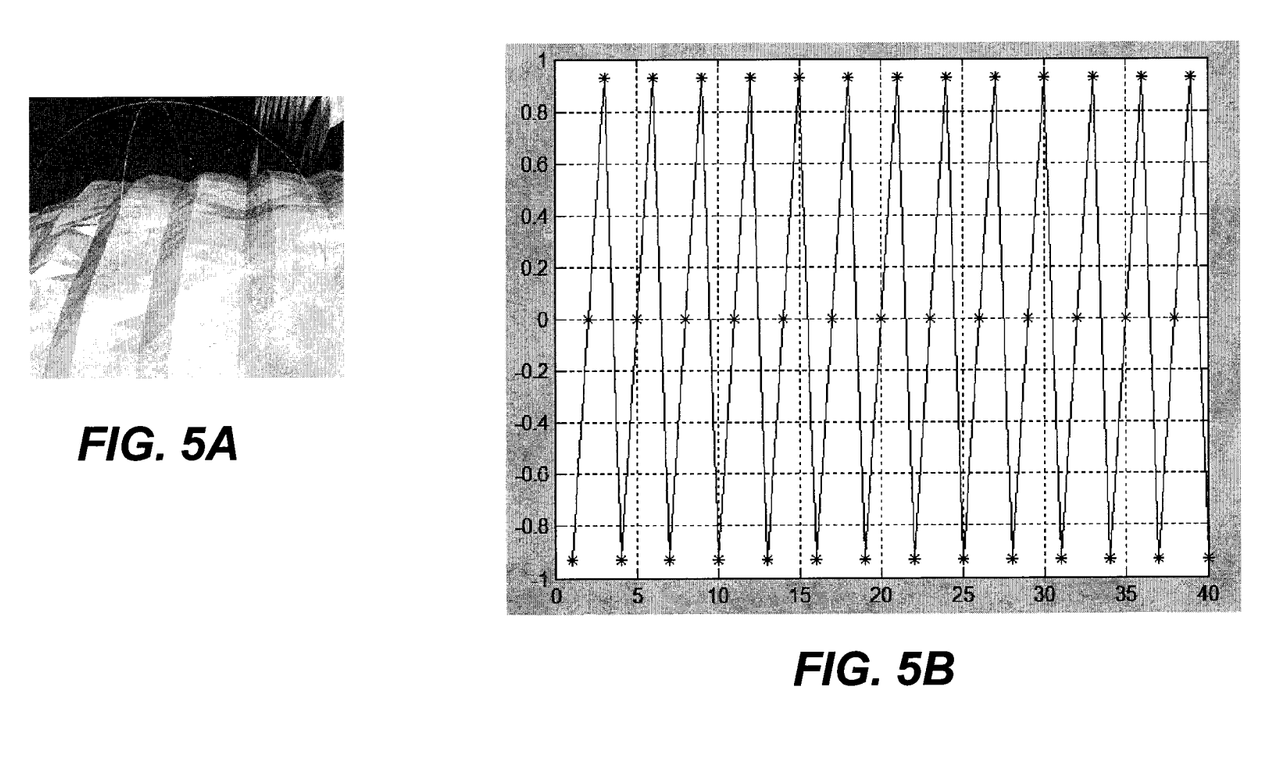
FIG. 5A shows a close-up view of sawtooth corrugations indicative of scanner movement during contour characterization using structured light.
FIG. 5B is a graph showing the normalized wave shape and periodicity of the projected structured light pattern.

The Applicants have developed exemplary method and/or apparatus embodiments for automatically detecting the sawtooth artifact of FIG. 4B. Referring to the close-up view of FIG. 5A, the sawtooth corrugations characteristic of motion during imaging are shown as they appear in close-up view. The corrugation spacing or periodicity appears to be related to the periodicity of the projected line pattern that is used for surface contour imaging and is apparent along a single direction only, along a direction that is orthogonal to the linear illumination features that are projected in parallel onto the surface. This orthogonal direction corresponds to the horizontal direction in the representation of FIG. 4B. FIG. 5B is a graph showing the normalized wave shape and periodicity (in units of mm along the horizontal axis).

The reconstructed image as shown in FIGS. 4A, 4B, and 5A is a range image, in which each surface pixel is assigned a position according to its detected distance from the intraoral camera sensor. A range image can be stored as a 2D matrix, in which each pixel stores a reconstructed 3D point. With this arrangement, a range image is stored as a set of well structured 3D points, with the same contour information represented by a mesh. The range image thus provides a useful arrangement of the contour information for processing and analysis.

Figure 6A:
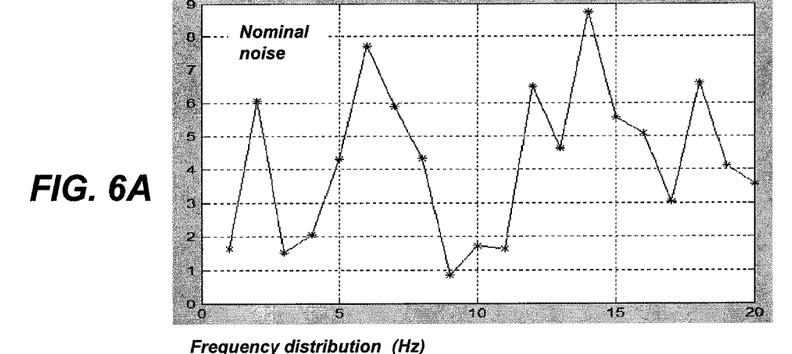
FIG. 6A is a graph that shows the characteristic frequency distribution for noise for a nominal image that is not perceptibly affected by scanner motion.

In analyzing the surface reconstruction, processing considers each row of pixels acquired at a time. FIG. 6A is a graph showing the characteristic frequency distribution for noise along a row (or line) of a nominal image that is not perceptibly affected by scanner motion and thus does not exhibit sawtooth features or surface corrugations. The vertical scale indicates noise energy in dimensional units (mm). As can be seen from FIG. 6A, noise is well distributed over the range of frequencies shown, from 0-20 Hz, with no apparent pattern.

Figure 6B:
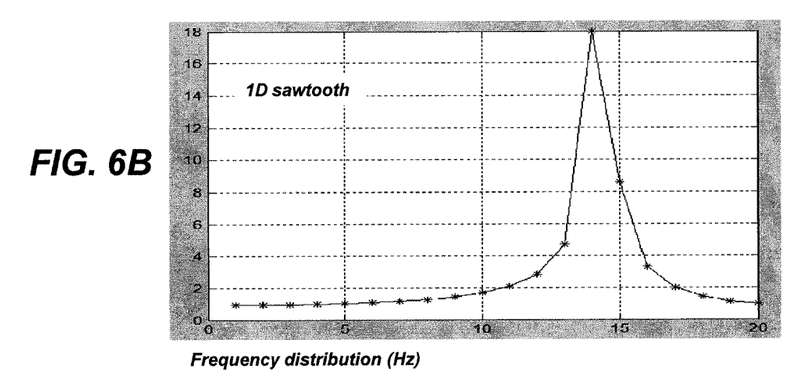
FIG. 6B is a graph that shows characteristic frequency distribution indicative of excessive motion.

By contrast with FIG. 6A, FIG. 6B is a graph showing the characteristic frequency distribution for an image that is perceptibly affected by scanner motion and exhibits sawtooth features or surface corrugations. It should be noted that the vertical scale of the FIG. 6B image differs from that shown in FIG. 6A by a factor of 2; a particular vertical distance in FIG. 6A represents half the energy change than does the same vertical distance in the FIG. 6B representation. Relative to noise content, the frequencies for surface reconstruction exhibiting sawtooth effects (FIG. 6B) are fairly distinctive and separable from the standard noise characteristics shown in FIG. 6A.

In order to evaluate image quality and to detect the presence of the sawtooth corrugations of FIGS. 4B and 5A, an embodiment of the present disclosure performs line-by-line (one-dimensional or 1D or row-by-row) analysis of the reconstructed volume. The line extends in the direction that exhibits the sawtooth corrugations, horizontal in the examples given herein.

Figure 7A:
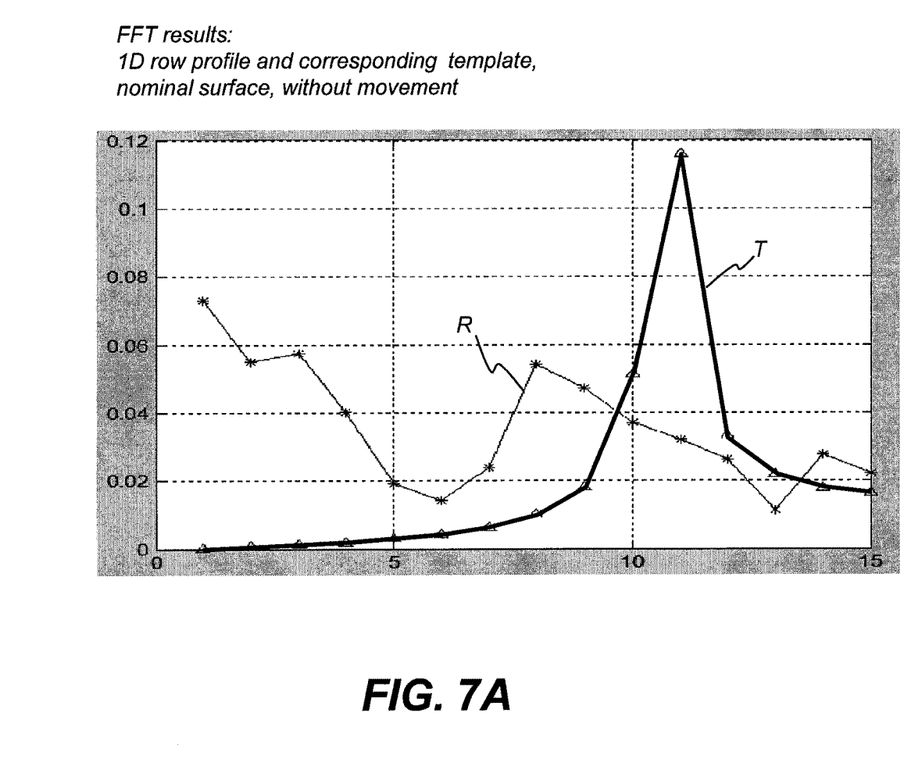
FIG. 7A is a graph showing Fast Fourier Transform (FFT) computation results for each row of pixels from a reconstructed range image.

The graph of FIG. 7A shows the results of Fast Fourier Transform (FFT) computation for each row of pixels from the reconstructed range image. A template is generated based on empirically determined characteristics of the sawtooth effect and is compared against actual data values for pixels along the row. A frequency-domain transform, such as FFT is applied both to the actual row value data and to the template; the two FFT results are compared against each other to calculate correlation coefficients. The FFT transform curve of template T is in bold, shown with the transform of row values R. In the example shown in FIG. 7A, the correlation coefficient is calculated at approximately 0.41.

Figure 7B:
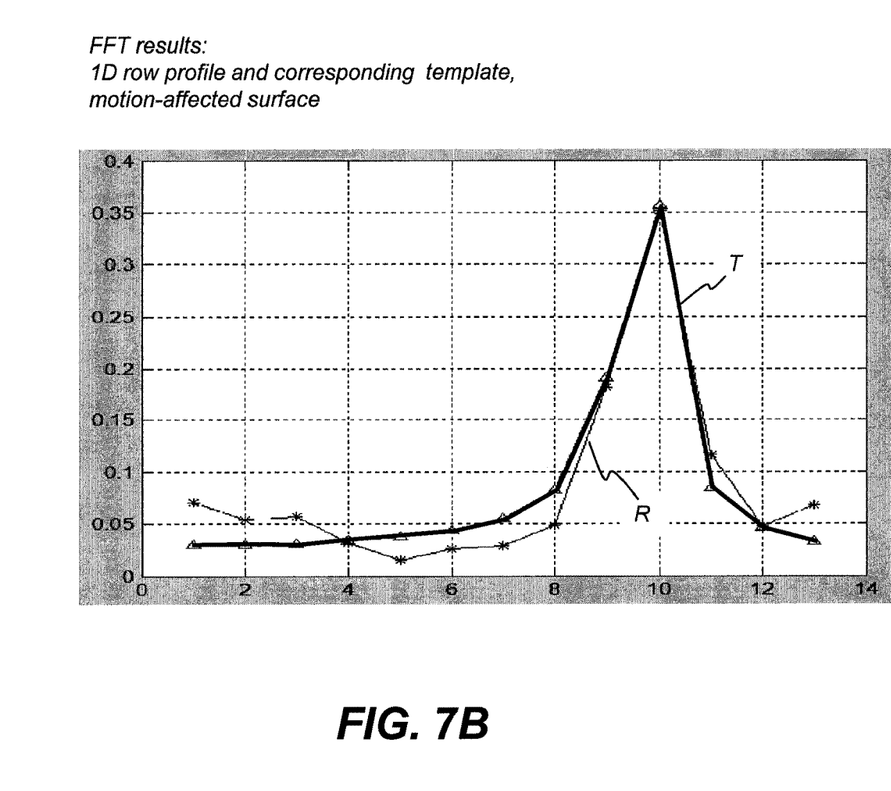
FIG. 7B is a graph that shows FFT results for a row of surface pixels where motion has been detected.

FIG. 7B shows FFT results for a row of surface pixels wherein motion during image acquisition has been detected. Here, the correlation coefficient is calculated at approximately 0.96.

Standard deviation (STD) can alternately be used to help distinguish the relative degree of movement energy that is reflected in the surface pixel data. Energy from pronounced motion will be more noticeable than energy from slight motion or vibration. Thus, the standard deviation provides a sensitive index of the sawtooth level.

Figure 8:
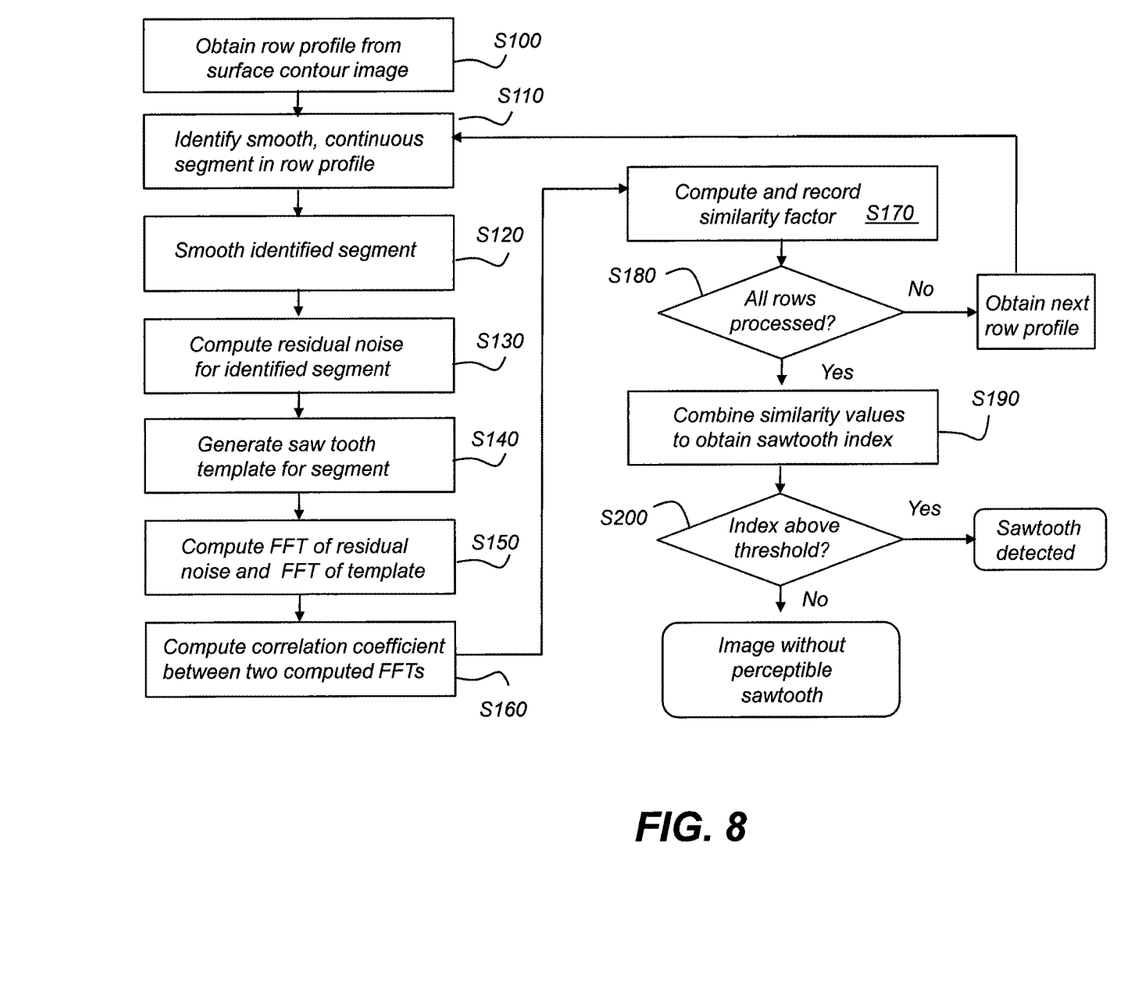
FIG. 8 is a logic flow diagram that shows a sequence for processing a range image using the characteristic relationships shown in FIGS. 6A-7B.

The logic flow diagram of FIG. 8 shows a sequence for processing a range image using the characteristic relationships shown in FIGS. 6A-7B. The process begins with a reconstructed surface contour image, such as a range image obtained using structured light. In a row profile acquisition step S100, a single row of pixels from the range image is identified for processing. A segment identification step S110 identifies a relatively smooth segment of the row as a useful candidate for analysis. According to an embodiment, step S110 processes pixel data to determine the segment of the row that is continuous and is smoother than any other segment from that row. According to an embodiment, step 110 searches for the longest continuous segment over which pixels do not exhibit obvious or pronounced fluctuation in detected distance from the intraoral camera sensor. A smoothing step S120 can use an averaging filter or other type of filter to further smooth the identified segment, such as to reduce high-frequency noise content. A noise computation step S130 computes the residual noise for the identified segment following the smoothing operation of step S120.

Continuing with the FIG. 8 processing sequence, a template generation step S140 generates a template for the sawtooth pattern. A template is a discrete sequence simulating the characteristic variation of the saw tooth pattern. By way of example, a typical sawtooth sequence can be generated as [−1, 0, 1, 0, −1, 0, 1]. Each period contains 3 points, corresponding to 3 multiline images in the structured line pattern.

In a frequency-domain computation step S150, one or more frequency-domain transforms such as fast Fourier transforms (FFT) are computed for the residual noise results of noise computation step S130 and for the template generated in template generation step S140. A correlation step S160 then computes the correlation between the two computed FFTs or other transforms. This correlation is used in a computation step S170 to compute a similarity factor.

Similarity factor computation can obtain the multiplicative product of the correlation coefficient and standard deviation (STD) of the residual noise obtained from step S130. Using the processing shown in FIGS. 6A-8, for example, a final similarity factor can be defined using:

Similarity Factor=Correlation Coefficient*STD(Input Row Profile)

In practice, it can be assumed that the correlation coefficients from a nominal surface obey some uniform distribution with zero mean value, since the residue from a nominal surface is generally random. Thus, the coefficient along rows can be averaged to help reduce the effect of a single row profile.

A looping step S180 then repeats the process for subsequent rows of the range image.

After all rows have been processed, a combination step S190 then combines the similarity factors for all of the rows in order to generate a single value that is indicative of the likelihood of the sawtooth artifact. In a test step S200, this value is measured against a predetermined threshold value, which can be empirically determined, in order to provide an indication that the sawtooth artifact has been detected or, alternately, that the reconstructed surface image does not exhibit this motion artifact.

Where the sawtooth artifact is detected, this detection is reported to the operator in some way, such as by indicating the status of the detection on display 26 (FIG. 1) or displaying a message or otherwise indicating to the operator or to subsequent processing routines that the image content is not satisfactory. Where image processing speeds permit, detection of excessive movement can be reported immediately to the operator during scanning by an audible tone or indicator light provided on the scanning camera itself or on a supporting display device. The generated range image that has been analyzed and exhibits this sawtooth effect can be discarded or may be further processed in order to reduce or correct for the motion problem.

The method of FIG. 8 can be applied to an entire surface as well as to a partial portion of the imaged surface that represents a region of interest.

According to an optional exemplary embodiment of the present disclosure, an imaging system or apparatus 100 (FIG. 1) for intraoral imaging has a scanner that acquires a plurality of images of a light pattern repeatedly projected onto a surface; a logic processor that executes programmed instructions for forming a range image from the acquired plurality of light pattern images and processes at least one row of pixels in the range image by: (i) computing residual noise in the row; (ii) generating a template for at least a segment of the row, wherein the template is characteristic of an imaging artifact related to motion; (iii) computing a similarity factor according to correlation between Fourier transforms of the template and computed residual noise; and (iv) comparing the computed similarity factor against a threshold to identify an image artifact. The imaging apparatus can have an audible or visual indicator in signal communication with the logic processor and energizable to report the image artifact or excessive motion.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as host processor 240 as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments according to the application can reduce or correct for inadvertent relative motion problems when 3D scanning a patient's dentition. Exemplary embodiments according to the application can include various features described herein (individually or in combination). Although embodiments of the present disclosure are illustrated using dental imaging apparatus, similar principles can be applied for other types of diagnostic imaging and for other anatomy.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

What is claimed is:

1. A method for intraoral imaging comprising:
   a) acquiring a plurality of structured light images from a region of interest and forming a range image that characterizes the surface contour of the region of interest according to the acquired structured light images;
   b) processing at least one row of pixels in the range image by:
      (i) selecting a segment of the row;
      (ii) computing residual noise in the selected segment;
      (iii) generating a template for the segment, wherein the template is characteristic of an imaging artifact related to motion;
      (iv) computing a similarity factor according to correlation between frequency-domain transforms of the template and computed residual noise;
      (v) comparing the computed similarity factor against a threshold to identify an image artifact;
   and
   c) reporting the image artifact or excessive motion.

2. The method of claim 1 wherein the image artifact relates to a sawtooth or corrugated surface effect.

3. The method of claim 1 wherein the image artifact results from unintended motion of a scanning apparatus.

4. The method of claim 1 further comprising smoothing the selected segment.

5. The method of claim 1 wherein the frequency-domain transform is a Fourier transform.

6. The method of claim 1 wherein the structured light images use a pattern of parallel lines.

7. The method of claim 1 wherein selecting comprises identifying a smooth continuous segment of the row.

8. The method of claim 1 wherein computing the similarity factor uses the standard deviation for the row.

9. The method of claim 1 wherein the structured light images show one or more teeth.

10. The method of claim 1 wherein the segment contains a plurality of sawtooth surface effects.

11. A method for intraoral imaging comprising:
    a) acquiring a plurality of structured light images from a region of interest and forming a range image that characterizes the surface contour of the region of interest according to the acquired structured light images;
b) processing at least one row of pixels in the range image by:
 (i) selecting a smoothly continuous segment of the row;
 (ii) smoothing the selected segment;
 (iii) computing residual noise in the smoothed, selected segment;
 (iv) generating a template for the segment, wherein the template is characteristic of an imaging artifact related to motion;
 (v) computing a similarity factor according to correlation between Fourier transforms of the template and computed residual noise;
 (vi) comparing the computed similarity factor against a threshold to identify an image artifact; and
c) reporting the image artifact or excessive motion.

12. An imaging apparatus for intraoral imaging comprising:
a) a scanner that acquires a plurality of images of a light pattern repeatedly projected onto a surface;
b) a logic processor that executes programmed instructions for forming a range image from the acquired plurality of light pattern images and processes at least one row of pixels in the range image by:
 (i) computing residual noise in the row;
 (ii) generating a template for at least a segment of the row, wherein the template is characteristic of an imaging artifact related to motion;
 (iii) computing a similarity factor according to correlation between Fourier transforms of the template and computed residual noise;
 (iv) comparing the computed similarity factor against a threshold to identify an image artifact; and
c) an audible or visual indicator in signal communication with the logic processor and energizable to report the image artifact or excessive motion.

* * * * *